United States Patent [19]
Donati et al.

[11] 3,937,789
[45] Feb. 10, 1976

[54] PROCESS FOR THE NEUTRALIZATION OF ACID SOLUTIONS OF CAPROLACTAM

[75] Inventors: Ivo Donati, Rieti; Werner Muench, Milan; Mario Fidecicchi, Torviscosa, all of Italy

[73] Assignee: Snia Viscosa Societa' Nazionale Industria Applicazioni Viscosa S.p.A., Milan, Italy

[22] Filed: Dec. 14, 1973

[21] Appl. No.: 425,171

Related U.S. Application Data

[63] Continuation-in-part of Ser. No. 31,343, April 23, 1970, abandoned, which is a continuation-in-part of Ser. No. 520,555, Jan. 14, 1966, abandoned.

[30] Foreign Application Priority Data
Jan. 21, 1975   Italy .................................. 1329/65

[52] U.S. Cl. .......................... 423/549; 260/239.3 A
[51] Int. Cl.² ....................................... C01C 1/242
[58] Field of Search ...... 423/549, 550; 260/239.3 R, 260/239.3 P, 239.3 A

[56] References Cited
UNITED STATES PATENTS

| | | | |
|---|---|---|---|
| 2,890,935 | 6/1959 | Lloyd ............................... | 423/549 |
| 3,117,964 | 1/1964 | Nirenberg ....................... | 260/239.3 A |
| 3,127,395 | 3/1964 | Landau .......................... | 260/239.3 A |
| 3,186,984 | 6/1965 | Coltow .......................... | 260/239.3 A |
| 3,264,060 | 8/1966 | Nieswandt ..................... | 260/239.3 A |

*Primary Examiner*—Earl C. Thomas
*Attorney, Agent, or Firm*—Shlesinger, Fitzsimmons & Shlesinger

[57] ABSTRACT

A process is disclosed in which the heat generated, during neutralization, by ammonium sulfate of a solution of $\xi$-caprolactam in sulfuric acid, is used to effect evaporation of water present, and the temperature is kept at about 40°C to 50°C, under subatmospheric pressure, so that substantial hydrolysis of the caprolactam is avoided while a substantial portion of the water present in the neutralization mixture is evaporated at the subatmospheric pressure, and the ammonium sulfate is crystallized substantially free from entrained caprolactam. The caprolactam is then separated from the aqueous phase.

5 Claims, 1 Drawing Figure

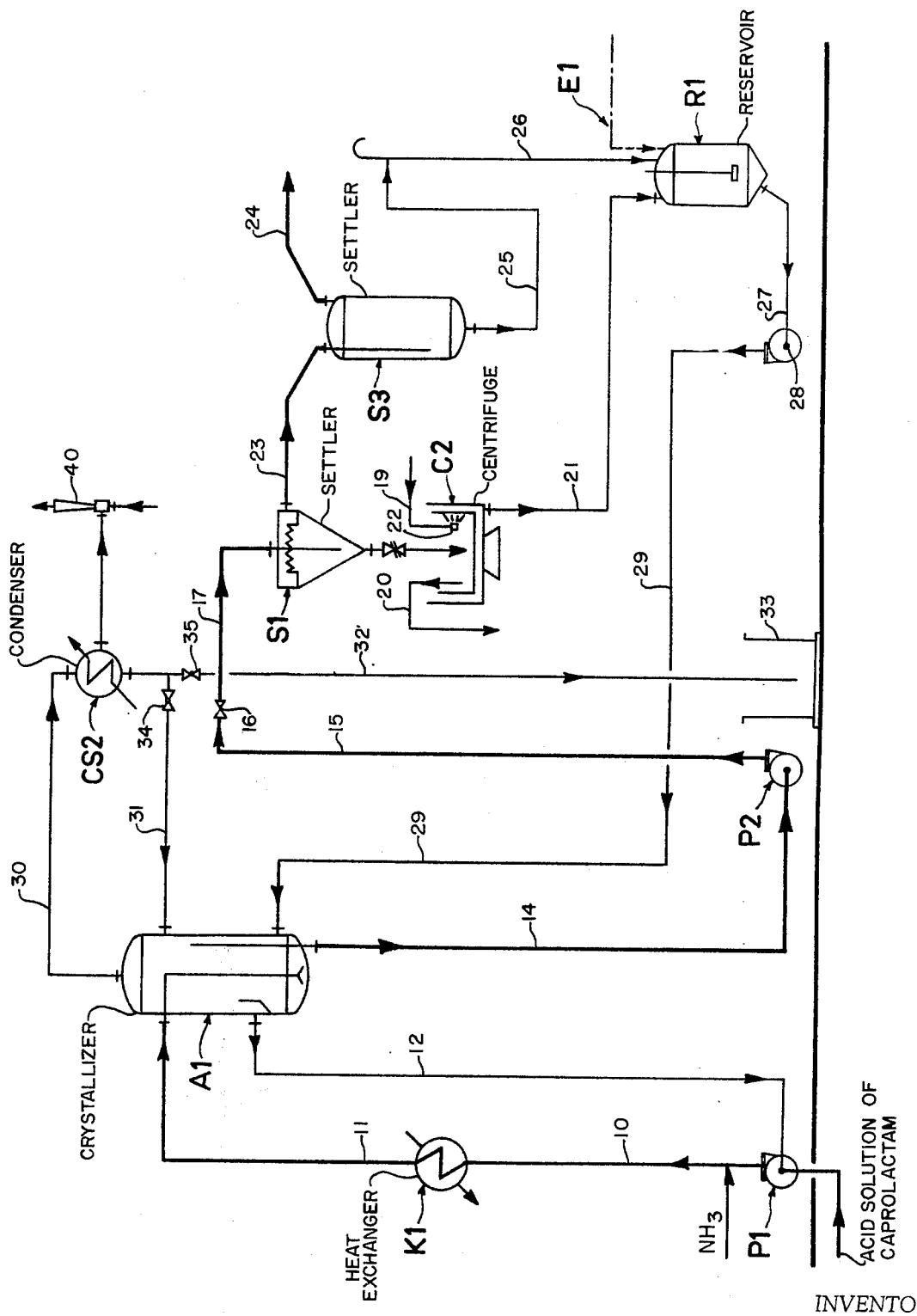

PROCESS FOR THE NEUTRALIZATION OF ACID SOLUTIONS OF CAPROLACTAM

This application is a continuation-in-part of our application Ser. No. 31,343 filed April 4, 1970 now abandoned, which in turn is a continuation-in-part of our application Ser. No. 520,555 filed Jan. 14, 1966, also now abandoned.

The present invention relates to an improvement in processes for neutralizing acid solutions of caprolactam.

Most processes for the production of caprolactam involve obtaining solutions of caprolactam in a strong acid, generally sulfuric acid, in concentrations which vary according to the method of preparation. In each case, these acid solutions must be neutralized before the caprolactam can be recovered. The neutralizer generally used is ammonia, and the ammonium sulfate, obtained as a by-product of the treatment in the case of acid solutions with sulfuric acid, has considerable commercial value.

To obtain satisfactory crystallization of the ammonium sulfate formed by the neutralization reaction and in order to separate the caprolactam, the system must contain some water.

In presently known processes for neutralization and separation of caprolactam from an ammonium sulfate solution, it has been considered necessary to prevent the precipitation of ammonium sulfate crystals in the presence of caprolactam oil because of the possible entrainment of part of the lactam present by part of the ammonium sulfate. In order to prevent such entrainment, it was considered necessary to carry out the entire neutralization process in steps, namely: neutralization of the acid solution and separation of the caprolactam oil in a first step, and thereafter, evaporation of the aqueous solution of ammonium sulfate and subsequent precipitation of the crystals of this salt in a second step.

This technique required first, neutralization of the acid solution of the caprolactam with ammonia under conditions which would prevent precipitation of the ammonium sulfate, and for this purpose the heat of reaction was removed by refrigerants in order to prevent the water from evaporating. At this point two liquid layers were obtained: an upper oily layer consisting essentially of caprolactam, and a lower aqueous layer formed by the aqueous solution of ammonium sulfate, which still held about 1% caprolactam in solution. The oily layer of caprolactam was separated from the aqueous layer, and the water in the latter was evaporated in order to permit the ammonium sulfate to crystallize. Multi-stage evaporating plants were ordinarily used in order to keep within economical limits the energy consumption required for this evaporation of the water, but these plants greatly increased the total cost of the process. The temperature in the successive stages of these plants rose to such high values that at the pH existing in the operation (about 4.5) roughly 1% of the caprolactam present was subject to hydrolysis, and for this reason, in general, it was necessary to extract the caprolactam from the aqueous solution of $(NH_4)_2SO_4$ with organic solvents before sending it on to the evaporator.

An object of the present invention is to devise an improved process in which the neutralization of the acid solution of caprolactam, the separation of the oily layer of caprolactam from the aqueous solution of ammonium sulfate, and the evaporation of the water are carried out in a single stage. Other objects will be obvious from the following description.

In the process of the invention, the neutralization and the evaporation of the water take place at subatmospheric pressure ranging from between about 0.055 and 0.095 atmospheres, and at low temperatures, no higher than about 40°–50°C, and the heat of reaction of the neutralization is utilized as the major source of heat for evaporating the $H_2O$.

Accordingly, the invention makes it possible to do the following:

1. utilize the heat of the exothermic reaction between the strong acid (usually sulfuric acid) and the ammonia, for use in evaporating a substantial amount of the water;
2. carry out the evaporation process at low temperature in a single stage, which is the preferred form of execution, and which is found to be advantageous after utilization of the heat of reaction;
3. carry out in a single stage the neutralization of the acid solution and the precipitation of the ammonium sulfate crystals, without allowing the latter to entrain any considerable amount of caprolactam;
4. avoid any hydrolysis phenomena and hence avoid the need for extracting the caprolactam from the aqueous solutions of ammonium sulfate before sending the solutions to evaporation;
5. carry out, in the preferred form of execution, the following operations in a single apparatus: neutralization of the acid solution of caprolactam, at subatmospheric pressure and low temperature, dissolution of the ammonium sulfate in water, evaporation of the water and crystallization of the $(NH_4)_2SO4$, and finally, separation of the caprolactam. The heat produced in the reaction at said pressure and temperature is such that the water evaporated in this single stage is in an amount at least three-fourths the amount of sulfuric acid concurrently neutralized.

Thus, with the present invention, from the exothermic reaction between sulphuric acid and ammonia (in se well known), there is developed a considerable amount of heat (also a well known phenomenon) which is exploited in this invention in the very reaction vessel itself for the evaporation (and not merely the heating) of an amount of water sufficient to cause the ammonium sulfate, which forms and is placed in solution, to crystallize and thus to separate from the liquid mass. The various steps are interconnected. The evaporation of a considerable amount of water in the reaction vessel (at least three-quarters of the amount of sulphuric acid) results from the fact that the evaporation takes place at relatively low temperature, which in turn means that the reaction environment must be maintained at low pressure; and the fact that this considerable amount of water is caused to evaporate leads to the obtaining, in this same reaction environment, of the crystallization, and thus the separation of the ammonium sulfate. All the water is eliminated by evaporation from the crystallizer without absorption of heat energy from the outside. This means that the heat generated by the neutralization is immediately absorbed by the change of state (evaporation) of the water, as this heat develops.

It is important to note that the amount of water that is evaporated in a unit of time is related to the amount of sulfuric acid that is neutralized in the same unit of time. The heat, which is continuously generated by the neutralization in other words is exploited to cause evaporation of a considerable amount of water. This contrasts with the prior known art, according to which there is merely exploitation of the residual heat possessed by the heated mass which is cooled slightly.

With the process of the present invention, moreover, the presence of water in the crystallizer is also important and advantageous. Crystallization from a good amount of water leads to formation of large, easily separable crystals. By feeding caprolactam in the presence of a large amount of water it is possible to use non-anhydrous caprolactam, which can be produced with commercially advantageous processes.

The essential difference between the present process and the prior art lies precisely in the "geographical" coincidence of the environment in which are carried out (a) the neutralization, (b) the elimination of the water at low pressure by evaporation and (c) the crystallization. Only as a result of this "geographical" coincidence does it become possible to exploit all of the heat produced by the reaction, for the purpose of evaporating the water. Furthermore, and again only as the result of this "geographical" coincidence is it possible to operate continuously at constant temperature because the reaction heat is absorbed by evaporation of the water or at least part of the water without having recourse, as was required in the prior art, to the subsequent steps of heating and cooling in order to store heat in the place where it was generated and then to transfer it to a "geographically" different place to utilize it.

The present invention makes possible the elimination of the following drawbacks which exist in known processes:

a. the possible loss of caprolactam with the solid phase (crystals of $(NH_4)_2SO_4$) from the concentrated solutions of ammonium sulfate separated from the lactam oil.

b. The possible loss of caprolactam with the vapor phase in the evaporation of the $H_2O$.

c. Excessive complexity of the evaporating plant. With the method of invention, the number of pieces of apparatus in the plant is greatly reduced.

The first drawback is avoided by washing, in a centrifuge with $H_2O$, crystals of $(NH_4)_2SO_4$ obtained from the concentrated solution of ammonium sulfate that is recovered.

The second drawback is eliminated by maintaining as low an operating temperature as possible (at 40°C about) in the reactor in which the operation is carried out.

The improved process of the present invention can be carried out advantageously in a plant including at least one neutralizer and one settler in several units, or else in a single unitary complex.

The process illustrated by the following examples was performed in apparatus which consisted essentially of the following items which are illustrated in the FIGURE of the attached drawing:

The crystallizer. A-1:

This is a vertical cylindrical vessel equipped with a circulation pump P 1.

This pump withdraws the mixture from the vessel through the pipe 12 at approximately one third of the height of the vessel and recycles it to the bottom of said vessel through the pipe 10 the heat exchanger K 1 and the pipe 11, which extends to the bottom of the vessel. The acid solution of caprolactam is fed to the suction side of the pump P1, whereas liquid ammonia is supplied to the delivery line 10. In such pipe 10, therefore, the acid solution of caprolactam, ammonia and the mother liquor recycled from the vessel mix together and reaction occurs between $NH_3$ and the acid solution. Because the neutralization reaction is exothermic, the temperature of the resulting mixture increases. The liquid mixture passes then through the heat exchanger K 1, pipe 11 and is delivered to the bottom of the vessel, as above described.

The crystallizer is kept at an absolute pressure of 0.06 ata. corresponding to a boiling point of about 43°C of the mother liquor. As a result, when the liquid mixture enters the crystallizer, it is subjected to a "flash" evaporation of water, followed by precipitation of ammonium sulfate crystals. The recycling of the mixture withdrawn from the vessel is adjusted so as to ensure that the three phases formed during the operation of the crystallizer, i.e., the lactam oil, the mother liquor (aqueous solution of $(NH_4)_2SO_4$); and solid ammonium sulfate, are completely mixed in the vessel.

The mixture is continuously extracted from the crystallizer at approximately ⅔ of its height by the pump P 2 connected to the vessel through the pipe 14.

A condenser $CS_2$ connected to the crystallizer by duct 30 provides for the condensation of the water evaporated in the crystallizer.

Downstream from said condenser there is provided a vacuum group, shown schematically in the FIGURE and consisting of a conventional ejector 40 diagrammatically illustrated at the right of the condenser $CS_2$. The water collected in the condenser can be recirculated to the crystallizer through duct 31 or delivered to a tank 33 through duct 32, depending upon the settings of the valves 34 and 35.

The first settler. S-1:

The extracted mixture passes from pump P 2 through conduit 15, valve 16 and conduit 17 into a conventional settler S-1, the upper part of which has a spillway for the mixture of two liquids, consisting of all the lactam oil and part of the mother liquor.

A turbid solution consisting of the crystallized salt and the remaining part of the mother liquor is tapped from the bottom of the settler.

The centrifuge C-2 is used for separating the ammonium sulfate from the mother liquor so as to obtain a practically dry salt. The centrifuge cake is washed with water from line 19, preferably demineralized water. The water is sprayed on the cake from a spray head 22 on line 19. The ammonium sulfate is carried off through a conduit 20; and the mother liquor passes through conduit 21 to the reservoir R1.

The second settler. S-3:

The mixture coming from the head of the first settler (S-1) passes through conduit 23 into a second conventional settler S-3, in which the lactam oil is separated from the mother liquor. The lactam oil is carried off from the settler S-3 through the discharge duct 24.

The mother liquor coming from the centrifuge C-2 through duct 21 and from the second settler S-3 through ducts 25 and 26 is collected in a reservoir R-1 and returned continuously to the crystallizer A-1 through duct 27, pump 28 and duct 29.

The following examples will illustrate the improved process of the present invention.

EXAMPLE 1 (FIG. 1)

A solution having the composition indicated below, and obtained in accordance with the known (e.g. U.S.P. 3,167,543) process of reacting hexahydrobenzoic acid with nitrosyl sulfuric acid, hydrolysis of the reaction mixture, and extraction of hexahydrobenzoic acid therefrom, has been made use of.

| Composition of the solution: | |
|---|---|
| Caprolactam (denoted by CL) | 12.75% |
| By-products (denoted by BP) | 2.55% |
| $H_2SO_4$ | 51.00% |
| $H_2O$ | 33.70% |

The recirculating pump P-1 is fed with 7.84 kg/h of a solution(4)containing:

| CL | 1 kg. |
|---|---|
| BP | 0.2 kg. |
| $H_2SO_4$ | 4 kg. |
| $H_2O$ | 2.64 kg. | and 1.35 kg/h of liquid $NH_3$ is supplied to the delivery line 10.

When these rates were kept constant, the pH measured in the recirculation stream was kept between 4.5 and 5.

The ejector 40 diagrammatically illustrated at the right of the condenser CS2, was regulated so as to maintain an absolute pressure of 0.06 atm. in the crystallizer, with corresponding temperatures of 43°C. in the liquid phase and 36°C in the vapor phase.

The following quantities of material were collected:

From the condenser CS-2 about 3 kg/h of water containing about 0.004 kg. of caprolactam;

From the second settler S-3, 1.593 kg/h of lactam oil containing 0.993 kg. of caprolactam, 0.2 kg. of by-products, and 0.4 kg. of water;

From the centrifuge C-2, 5.35 kg/h of ammonium sulfate, with 0.052 kg/h of $H_2O$ and 0.0025 kg/h of caprolactam. The washing of the cake on the centrifuge was carried out with about 0.8 kg/h of demineralized water. The mother liquors collected is the mother reservoir R-1 were recirculated, and their flow rate was about 20.36 kg/h.

The evaporation of the water within the crystallizer took place without any consumption of steam from the exchanger K-1.

EXAMPLE 2

A solution of epsilon caprolactam in sulfuric acid as obtained in a conventional manner by reaction of cyclohexanone and hydroxylamine sulfate, and having the following composition has been made use of:

| Caprolactam (denoted by CL) | 43.25% |
|---|---|
| By-products (denoted by BP) | 0.53% |
| $H_2SO4$ | 56.22% |

The recirculating pump P-1 is fed(3)2.312 kg/h of a solution containing:

| CL | 1.00 kg. |
|---|---|
| BP | 0.012 kg. |
| $H_2SO4$ | 1.300 kg. | and 0.44 kg/h of liquid $NH_3$ is fed to the delivery line 10.

Before continuous operation was started, the crystallizing apparatus was charged with an appropriate mixture of caprolactam in water (2.102 kg dissolved in 8.600 kg. of water) which is recirculated when continuous operation begins.

The pH, temperature, and pressures were the same as in the previous example.

All of the water condensed in CS-2 was recirculated into the crystallizer A-1.

The following quantities of material were collected:

From the second settler S-3, 1.422 kg/h of lactam oil containing 0.9992 kg. of CL, 0.012 kg. of BP, 0.4 kg of $H_2O$ and 0.01 kg. of ammonium sulfate;

From the centrifuge C-2, 1.73 kg/h of ammonium sulfate, with 0.0008 kg/h of CL and 0.017 kg/h of $H_2O$. The washing of the cake on the centrifuge was carried out with about 0.25 kg/h of demineralized water.

Through an auxiliary inlet E-1, 0.153 kg/h or water is fed into the reservoir R-1 in order to restore the balance of water in the plant.

The mother liquors collected in the reservoir R-1 were recirculated at a flow rate of 7.7 kg/h.

The steam from the heat exchanger K-1 is not utilized. The heat of reaction is utilized in order to ensure the heat balance of the process.

EXAMPLE 3

The caprolactam solution treated in the example was identical with that used in Example 2 above.

In this case, to introduce into the cyrstallizer the water necessary for satisfactorily crystallizing the $(NH_4)_2SO4$, the process uses an aqueous solution of ammonium sulfate obtained from a previous phase of the preparation of caprolactam, i.e., from the preparation of the oxime.

The pump was supplied with the acid solution and the liquid $NH_3$ was supplied to line 10 at the same flow rate as those disclosed in Example 2 above.

In addition, the reservoir R-1 was fed with 7.03 kg/h of an ammonium sulfate solution coming from the syntheses of the oxime and containing 4.36 kg. of $H_2O$ and 2.67 kg. of salt. This amount was added through the inlet E-1.

The pressures, temperatures and pH were identical with those of the previous Examples.

The following quantities of material were collected:

From the condenser CS-2, 4.556 kg/h water containing 0.006 kg of CL;

From the second settler S-3, 1.422 kg/h of oil, containing: 0.992 kg of caprolactam, 0.012 kg of BP, 0.004 kg of $H_2O$ and 0.01 kg of ammonium sulfate;

From the centrifuge C-2, 4.40 kg/h of ammonium sulfate with 0.002 kg/h of CL and 0.040 kg/h of $H_2O$. The washing of the cake in the centrifuge was carried out with 0.63 kg/h of demineralized $H_2O$.

The mother liquors collected in the reservoir R-1 were recirculated, at a flow rate of 26.23 kg/h.

The consumption of steam coming from the exchanger K-1 was 3.64 kg/h, which amounted ot 0.825 kg of steam per kilogram of salt crystallized, thus restoring the total heat balance of the plant to the most favorable conditions, due regard being paid to the fact that provision was also made for the separation of the ammonium sulfate introduced with the aqueous solution of the reservoir R-1.

Control analyses were made for the presence of caprolactam in the ammonium sulfate crystals obtained either by means of solution obtained in the process wherein hexahydrobenzoic acid is reacted with nitrosylsulfuric acid or by using the solution from the classical oxime process, and it was found that when the ammonium sulfate crystals were washed in the centrifuge with small amount of demineralized water, the caprolactam content of the crystals was less than 0.05% corresponding to the loss of about 0.3% or less in the case of the process proposed by applicants in accordance with the U.S. Pat. No. 3,022,291 and to a loss of less than 0.1% in the case of the classical oxime process.

Having thus described our invention, what we claim is:

1. In a process for neutralizing a solution of $\xi$ caprolactam in sulfuric acid wherein neutralization is effected with ammonia, and the ammonium sulfate, formed as a result of the neutralization is subsequently recovered in the presence of water, the improvement comprising feeding into a reaction vessel an aqueous solution of $\xi$-caprolactam in sulfuric acid, and a quantity of liquid ammonia sufficient to neutralize all the sulfuric acid, holding this mixture, including the water which is present, in this same vessel under subatmospheric pressure sufficient to maintain said vessel at a temperature of about 40°C to 50°C, and utilizing the heat evolved by the exothermic reaction between the sulfuric acid and the ammonia to effect in said same vessel, simultaneously with the neutralization of the sulfuric acid by the ammonia, evaporation of the water present in said vessel, in an amount at least three-fourths the amount of sulfuric acid concurrently neutralized, and consequent crystallization in said vessel of the produced ammonium sulfate, so that substantial hydrolysis of the caprolactam is avoided while a substantial portion of the water present in the mixture is being evaporated and the ammonium sulfate is allowed to crystallize in said vessel substantially free from the caprolactam, and drawing off the evaporated water from said same reaction vessel, separating the caprolactam from the remaining mother liquor, and separating the ammonium sulfate also from said mother liquor.

2. A process as described in claim 1, in which the caprolactam oil is separated from the mother liquor prior to separation of the crystallized ammonium sulfate from the said mother liquor.

3. A process as described in claim 1 in which the heat of neutralization constitutes the sole source of heat supplied to the mass to effect the evaporation of water therefrom.

4. A process as described in claim 1 in which heat of neutralization constitutes the major source of heat, a minor portion of the heat being supplied from an outside source.

5. In a continuous process for neutralizing a sulfuric acid solution of caprolactam, with liquid ammonia, by feeding a solution of caprolactam in sulfuric acid mixed with liquid ammonia into a reaction vessel, the improvement comprising during the neutralization of said solution continuously maintaining the reaction vessel and the neutralization mass substantially in the temperature range of from about 40°C to about 50°C and under an absolute pressure of between about 0.055 and 0.095 atmospheres, while using the heat evolved during the neutralization reaction to effect in said vessel evaporation at the subatmospheric pressure of a sufficient part of the water present to effect crystallization of said ammonium sulfate in said vessel, continuously removing from the reaction vessel the evaporated portion of the water content of the neutralization mass, the lactam oil, the crystallized ammonium sulfate, and the mother liquor, continuously separating the caprolactam as an oil phase from the aqueous ammonium sulfate layer which contains ammonium sulfate crystals, centrifuging the ammonium sulfate slurry, washing the ammonium sulfate crystals with cold water thereby to remove all but an inconsequential amount of caprolactam contained therein, and continuously recycling the combined mother liquors and wash liquors to the reaction vessel.

* * * * *

UNITED STATES PATENT OFFICE
CERTIFICATE OF CORRECTION

Patent No. 3,937,789     Dated February 10, 1976

Inventor(s) Ivo Donati, Werner Muench & Mario Fidecicchi

It is certified that error appears in the above-identified patent and that said Letters Patent are hereby corrected as shown below:

On the title page of the patent, in the foreign application priority data headed by the INID number [30], "Jan. 21, 1975" should read -- Jan. 21, 1965 --.

In column 1, line 5, "April 4," should read -- April 23,--.

Signed and Sealed this twenty-seventh Day of April 1976

[SEAL]

Attest:

RUTH C. MASON
Attesting Officer

C. MARSHALL DANN
Commissioner of Patents and Trademarks